(12) United States Patent
Steynberg et al.

(10) Patent No.: US 7,432,310 B2
(45) Date of Patent: Oct. 7, 2008

(54) PROCESS FOR SYNTHESISING HYDROCARBONS

(75) Inventors: André P. Steynberg, Vanderbijlpark (ZA); Jacob W. De Boer, Pretoria (ZA); Herman G. Nel, Sasolburg (ZA); Werner S. Ernst, Secunda (ZA); Johannes J. Liebenberg, Pretoria (ZA)

(73) Assignee: Sasol Technology (Proprietary) Limited, Rosebank, Johannesburg (ZA)

( * ) Notice: Subject to any disclaimer, the term of this patent is extended or adjusted under 35 U.S.C. 154(b) by 172 days.

(21) Appl. No.: 10/569,116

(22) PCT Filed: Aug. 20, 2004

(86) PCT No.: PCT/IB2004/051514

§ 371 (c)(1),
(2), (4) Date: Oct. 13, 2006

(87) PCT Pub. No.: WO2005/019384

PCT Pub. Date: Mar. 3, 2005

(65) Prior Publication Data

US 2007/0142481 A1    Jun. 21, 2007

Related U.S. Application Data

(60) Provisional application No. 60/497,364, filed on Aug. 22, 2003.

(51) Int. Cl.
*C07C 27/00* (2006.01)
*C07C 2/56* (2006.01)
*C10G 47/02* (2006.01)

(52) U.S. Cl. .................. 518/706; 518/705; 585/709; 208/108

(58) Field of Classification Search ............. 518/705, 518/706; 585/709; 208/108
See application file for complete search history.

(56) References Cited

U.S. PATENT DOCUMENTS 4,833,170 A    5/1989   Agee
6,156,809 A    12/2000  Clark et al.

*Primary Examiner*—Jafar Parsa
(74) *Attorney, Agent, or Firm*—Senniger Powers LLP

(57) ABSTRACT

A process (10) for synthesising hydrocarbons includes feeding a gaseous feedstock (18) comprising hydrogen and carbon monoxide, into a first Fischer-Tropsch reaction stage (12) which is a three-phase low temperature catalytic Fischer-Tropsch reaction stage, and allowing the hydrogen and carbon monoxide partially to react catalytically in the first reaction stage (12) to form hydrocarbons. At least a portion of a tail gas (32) which includes unreacted hydrogen and carbon monoxide obtained from the first reaction stage, is fed into a second Fischer-Tropsch reaction stage (42) which is a two-phase high temperature catalytic Fischer-Tropsch reaction stage. The hydrogen and carbon monoxide are allowed at least partially to react catalytically in the second reaction stage (42) to form gaseous hydrocarbons.

20 Claims, 2 Drawing Sheets

PROCESS FOR SYNTHESISING HYDROCARBONS

Figure 1:
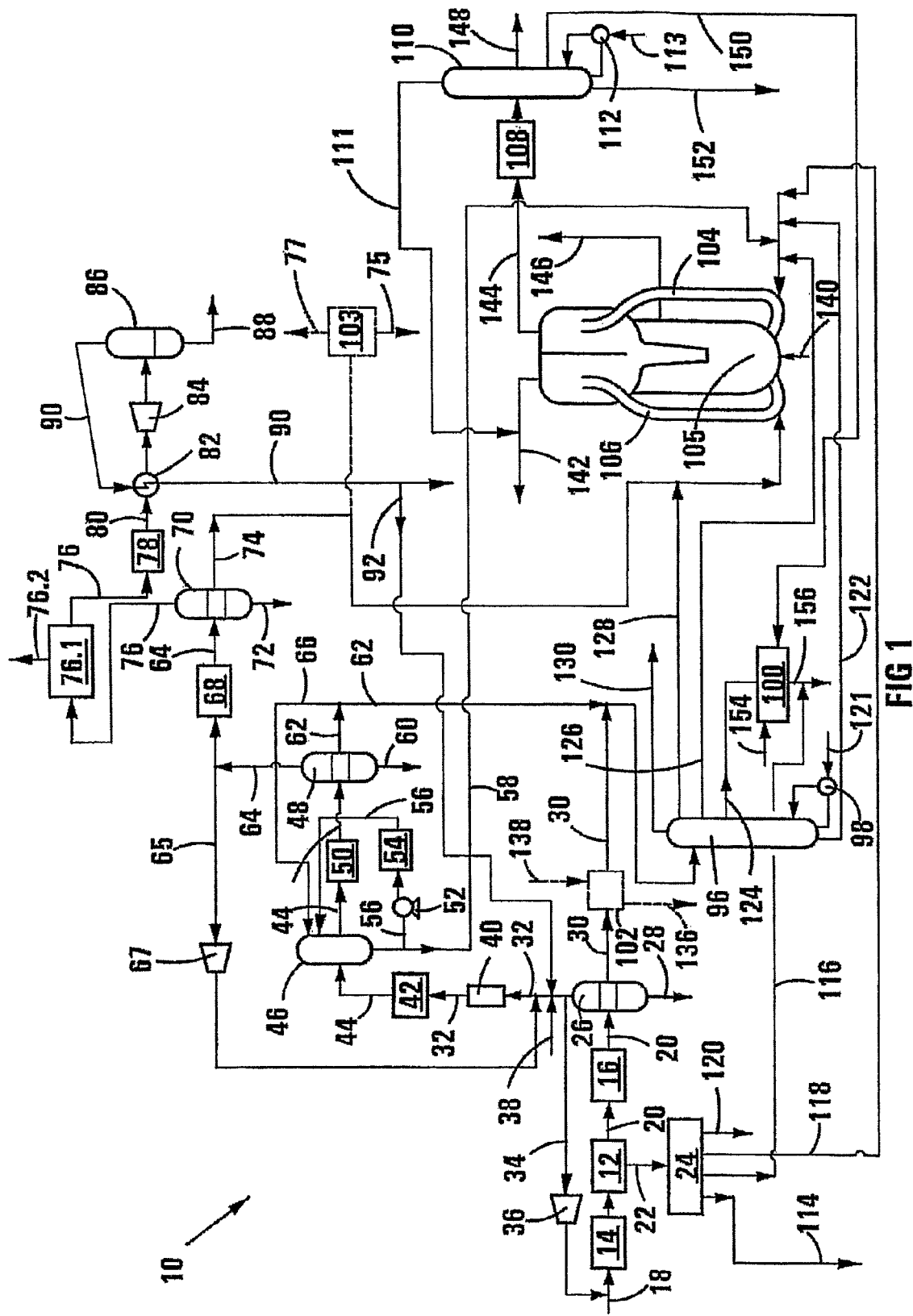

This application claims the benefit of U.S. Provisional Application Ser. No. 60/497,364, filed Aug. 22, 2003.

THIS INVENTION relates to hydrocarbon synthesis. It relates in particular to a process for synthesising hydrocarbons.

According to the invention, there is provided a process for synthesising hydrocarbons, which process includes feeding a gaseous feedstock comprising hydrogen and carbon monoxide, into a first Fischer-Tropsch reaction stage which is a three-phase low temperature catalytic Fischer-Tropsch reaction stage;

allowing the hydrogen and carbon monoxide partially to react catalytically in the first reaction stage to form hydrocarbons;

feeding at least a portion of a tail gas which includes unreacted hydrogen and carbon monoxide obtained from the first reaction stage, into a second Fischer-Tropsch reaction stage which is a two-phase high temperature catalytic Fischer-Tropsch reaction stage; and allowing the hydrogen and carbon monoxide at least partially to react catalytically in the second reaction stage to form gaseous hydrocarbons.

Typically, the first reaction stage includes a slurry bed of a solid particulate Fischer-Tropsch catalyst suspended in a carrier liquid, with the gaseous feedstock entering the slurry bed at a low level.

When employing a slurry bed in the first reaction stage, the hydrogen and carbon monoxide react catalytically as they pass upwardly through the slurry bed, thereby to form liquid hydrocarbon products and gaseous products, with the liquid hydrocarbon products thus constituting the carrier liquid of the slurry bed.

The process typically includes withdrawing liquid hydrocarbon products and gases and vapours from the first reaction stage, cooling the gases and vapours to condense liquid hydrocarbons and reaction water present therein and to produce the tail gas comprising the unreacted hydrogen and carbon monoxide obtained from the first reaction stage. Typically, the condensed liquid hydrocarbons, reaction water and tail gas are separated in, and withdrawn from, a separator vessel, with the withdrawn tail gas being fed to the second reaction stage.

The tail gas from the first reaction stage thus typically includes unreacted hydrogen, unreacted carbon monoxide and gaseous products which have formed in the first reaction stage, including $CO_2$, and which have not been condensed and separated from the tail gas. This tail gas typically includes small quantities of $C_5-$ hydrocarbons. Thus carbon dioxide will be formed in the first reaction stage by the water gas shift reaction.

The process may include adjusting a ratio of $H_2/(2CO+3CO_2)$ in the first stage tail gas, prior to feeding the adjusted first stage tail gas to the second reaction stage. Preferably, the ratio $H_2/(2CO+3CO_2)$ in the first stage tail gas fed to the second reaction stage is between 0.8 and 1.05.

In one embodiment of the invention, the ratio $H_2/(2CO+3CO_2)$ is adjusted by the addition of an $H_2$ rich gas to the first stage tail gas, e.g. an $H_2$ rich gas obtained by steam reforming of methane.

In another embodiment of the invention, the ratio $H_2/(2CO+3CO_2)$ is adjusted by removing excess $CO_2$ from the first stage tail gas recycle.

In a further embodiment of the invention, the ratio $H_2/(2CO+3CO_2)$ is adjusted by shifting some of the CO in the first stage tail gas by reaction with steam to produce $H_2$ and $CO_2$, in accordance with the water gas shift reaction $CO+H_2O<->CO_2+H_2$. Excess $CO_2$ may thereafter be removed prior to feeding the adjusted first stage tail gas to the second reaction stage.

In yet a further embodiment of the invention, the ratio $H_2/(2CO+3CO_2)$ is adjusted by the addition of an H rich gas to the first stage tail gas in combination with the reverse water gas shift reaction to convert excess $CO_2$ to CO.

The gaseous hydrocarbons and any unreacted hydrogen, unreacted carbon monoxide and any gaseous by-products, such as $CO_2$, are withdrawn from the second reaction stage, and may be separated into one or more condensed liquid hydrocarbon streams, a reaction water stream and a second stage tail gas.

The Fischer-Tropsch catalyst used in the first reaction stage may be a shifting catalyst, e.g. an iron catalyst, and is preferably a promoted iron catalyst. Typically, the catalyst is a precipitated catalyst. The catalyst may be promoted for activity and/or selectivity. It is however known that a reaction stage using promoted iron Fischer-Tropsch catalyst suffers from a rapid decline in reaction stage productivity as the per pass conversion of CO and $H_2$ increases. Advantageously, the first reaction stage may thus be operated with a low per pass conversion of CO and $H_2$ of between about 30% and about 50%.

By 'shifting catalyst' is meant a hydrocarbon synthesis catalyst which, at the operating conditions of the hydrocarbon synthesis process of the invention, converts more than 2% of CO passing through a reaction stage into $CO_2$.

The process may include recycling some of the first stage tail gas to the first reaction stage. The first stage tail gas recycle may be used to increase overall first stage CO and $H_2$ conversion to a value of no more than about 65%, preferably to a value of no more than about 60%, more preferably to a value of no more than about 50%. The gaseous feedstock to first stage tail gas recycle ratio, when recycle is used, will typically be about 1:1, but may vary depending on the gaseous feedstock composition; this ratio is however unlikely to exceed about 2:1.

The process may include recycling some of the second stage tail gas to the second reaction stage, to obtain high second reaction stage overall CO and $CO_2$ conversions. For the second reaction stage, overall $CO+CO_2$ conversion may be at least 65%, preferably at least 80%, more preferably at least 85%. The ratio of the first stage tail gas feed to the second reaction stage to the second reaction stage tail gas recycle will typically be about 1:1, but may vary depending on the first stage tail gas feed composition to the second reaction stage. This recycle ratio is unlikely to exceed about 2:1.

The first reaction stage may operate at a temperature of less than 280° C. Typically, the first reaction stage operates at a temperature of between 160° C. and 280° C., preferably between 220° C. and 260° C., e.g. about 250° C. The first reaction stage is thus a high chain growth, typically slurry bed, reaction stage, operating at a pre-determined operating pressure in the range 10-50 bar.

The second reaction stage may operate at a temperature of at least 320° C. Typically, the second reaction stage operates at a temperature of between 320° C. and 350° C., e.g. about 350° C., and at an operating pressure in the range 10-50 bar.

The second reaction stage is thus a low chain growth reaction stage, which typically employs a two-phase fluidised bed reactor. In contrast to the first reaction stage, which may be characterised by its ability to maintain a continuous liquid product phase in its slurry bed reactor, the second reaction stage can not produce a continuous liquid product phase in the fluidised bed reactor.

The Fischer-Tropsch catalyst used in the second reaction stage may be a shifting catalyst, e.g. an iron catalyst, and is preferably a promoted iron catalyst. The catalyst is typically a fused catalyst. The same type of catalyst may be used in the first and second reaction stages; however, the composition and quantity of the promoters and the catalyst physical properties e.g. density, will typically be different for the first and second reaction stages.

The gaseous feedstock to the first reaction stage may comprise hydrogen and carbon monoxide in a molar ratio of between about 0.4 and about 2.4, preferably between about 0.7 and about 2.0. Thus, preferably, there is an excess CO above the stoichiometric requirements for hydrocarbon synthesis, to suppress the undesirable formation of methane and to enhance or promote the production of desired olefinic hydrocarbon products in the first reaction stage.

The process may include forming $C_5-$ hydrocarbons in the first and the second reaction stages, passing the $C_5-$ hydrocarbons formed in the first reaction stage to the second reaction stage and recovering $C_5-$ hydrocarbons from the second reaction stage.

The process thus preferably includes a separation stage to separate light hydrocarbons, e.g. $C_2-C_4$ hydrocarbons and a $C_5+$ hydrocarbon stream from the second stage tail gas. 1-hexene may be separated from this $C_5+$ hydrocarbon stream. These separated light hydrocarbons may be used to produce ethylene, propylene and butylene products. The separation stage may also be used to separate light hydrocarbons from other streams produced in the process for synthesising hydrocarbons.

The liquid hydrocarbon product from the first reaction stage may comprise pre-dominantly wax. In other words, at least about 50% by mass of the liquid hydrocarbon product from the first reaction stage may be made up of $C_{19}+$hydrocarbons. This wax may be processed in a wax processing stage to give high yields of high quality lubricant base oil products and/or high value wax products. The wax processing stage may also yield a naphtha by-product, e.g. a $C_5-C_{10}$ naphtha by-product, a diesel product, e.g. a $C_{11}-C_{19}$ diesel product, and a heavier than diesel hydrocarbon product, e.g. a $C_{20}+$ hydrocarbon product. The wax may thus be worked up to produce one or more of diesel, naphtha, lubricants or speciality wax.

The process may include treating the condensed liquid hydrocarbons from the first reaction stage, and/or the condensed liquid hydrocarbons from the second reaction stage, to provide hydrocarbon fractions, e.g. a $C_5-C_8$ naphtha fraction, a $C_9-C_{13}$ hydrocarbon fraction, a diesel fraction and a light gas fraction.

A $C_9-C_{13}$ hydrocarbon fraction (an olefins containing stream) from the condensed liquid hydrocarbons from the first reaction stage may be treated to remove oxygenated hydrocarbons and then alkylated and subjected to a separation stage to produce linear alkyl-benzene and optionally $C_9-C_{13}$ paraffins. The process may thus produce linear alkyl-benzene as a product. In this case the remaining separated components from the condensed liquid hydrocarbons from the first reaction stage may be combined with separated hydrocarbon fractions from the second reaction stage and treated in an appropriate way.

The process may employ a fluidised catalytic cracker riser reactor to treat one or more of the naphtha products to produce an olefin product comprising propylene with ethylene and gasoline as the main by-products.

A catalytic cracker may be used to produce gasoline from heavier hydrocarbons produced as an intermediate product. Thus, the process may also employ a fluidised catalytic cracker riser reactor to treat heavier than diesel products ($C_{20}+$ hydrocarbons) to produce a gasoline containing product, which may be treated to provide gasoline and a diesel product.

A COD unit (Conversion of Olefins to Diesel unit) may be used to oligomerise olefins produced in the process of the invention thereby to enhance diesel production. The COD unit may include a reactor containing a zeolite catalyst capable of oligomerising naphtha to produce a diesel product with a paraffinic naphtha by-product.

The process may include a diesel hydrotreater stage to produce high quality diesel motor fuel from one or more diesel products produced by the process of the invention.

The process may produce a wax stream which makes up at least 10% by weight of all hydrocarbons produced by the process.

The process may produce LP gas, naphtha and diesel as intermediate or primary products.

The process may have a methane selectivity of no more than 20% and an overall CO and $CO_2$ conversion of at least 70%.

The invention will now be described, by way of example only, with reference to the accompanying diagrammatic drawings and the Example.

BREIF DESCRIPTION OF DRAWING

Figure 2:
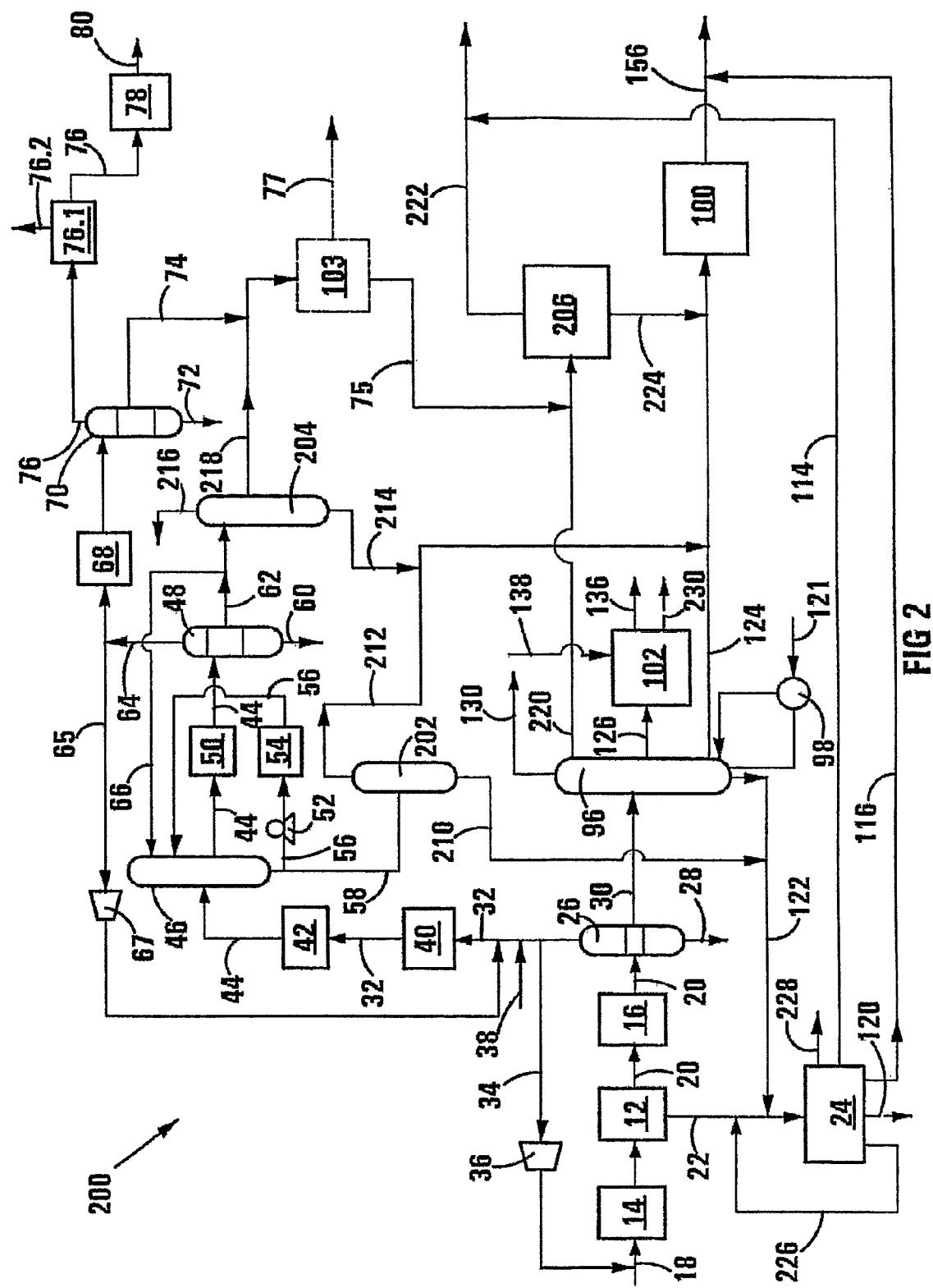

FIG. 1 shows one embodiment of a process in accordance with the invention for synthesising hydrocarbons; and FIG. 2 shows another embodiment of a process in accordance with the invention for synthesising hydrocarbons.

Referring to FIG. 1, reference numeral 10 generally indicates a process in accordance with the invention for synthesising hydrocarbons. The process 10 shown in FIG. 1 is suitable for use with a natural gas feedstock but can be used, with some modification, with a gaseous feedstock which is derived from a carbonaceous material, such as coal.

The process 10 includes a first Fischer-Tropsch reaction stage 12 preceded by an optional heater 14 and followed by a cooler 16. A gaseous feedstock line 18 feeds into the heater 14 and leads from the heater 14 to the first reaction stage 12. From the first reaction stage 12 a gaseous product line 20 leads to the cooler 16 and a liquid product line 22 leads to a wax processing stage 24.

The cooler 16 is followed by a separator 26 and is in flow communication with the separator 26 by means of the gaseous product line 20. From the separator 26, a reaction water line 28, a hydrocarbon condensate line 30 and a first stage tail gas line 32 lead. A first stage tail gas recycle line 34 leads from the first stage tail gas line 32 back to the gaseous feedstock line 18, via a compressor 36. An $H_2$ rich gas line 38 feeds into the first stage tail gas line 32.

The first stage tail gas line 32 leads into an optional heater 40 and from the heater 40 into a second Fischer-Tropsch reaction stage 42. A gaseous product line 44 leads from the second reaction stage 42 to a washing column 46 and from the washing column 46 to a separator 48, via a cooler 50.

The washing column 46 is provided with a pump 52 and a cooler 54, both located in a heavy oil recycle line 56. The heavy oil recycle line 56 is taken from a heavy oil line 58 leading from the bottom of the washing column 46.

A reaction water line 60, a hydrocarbon condensate line 62 and a second stage tail gas line 64 lead from the separator 48.

A hydrocarbon condensate reflux line 66 is taken from the hydrocarbon condensate line 62 and leads back into the washing column 46.

The second stage tail gas line 64 leads into a refrigeration stage 68 and from there into a separator 70. A tail gas aqueous condensate line 72, a tail gas hydrocarbon condensate line 74 and a wet tail gas line 76 leave the separator 70. The wet tail gas line 76 feeds into a $CO_2$ removal stage 76.1 provided with a CO removal line 76.2. From the $CO_2$ removal stage 76.1 the wet tail gas line 76 feeds into a dryer 78. From here, a dry tail gas line 80 passes through a heat exchanger 82 and an expansion turbine 84 into a separator 86. A light hydrocarbon line 88 and a lean tail gas line 90 leave the separator 86, the lean tail gas line 90 passing through the heat exchanger 82. An optional recycle line 92 branches off from the lean tail gas line 90. The tail gas hydrocarbon condensate line 74 may optionally lead to a 1-hexene recovery stage 103, from which a 1-hexene lean hydrocarbon line 75 and a 1-hexene product line 77 lead.

From the second stage tail gas line 64, a second stage tail gas recycle line 65 returns to the first stage tail gas line 32, via a compressor 67.

The process 10 further includes an optional oxygenate removal and olefin conversion stage 102 to react $C_9$-$C_{13}$ olefins with benzene to produce linear alkylbenzene, a distillation column 96 with a steam reboiler 98, a diesel hydrotreater stage 100, a first fluidised catalytic cracker riser reactor 104, a second fluidised catalytic cracker riser reactor 106, a cooler 108 and a distillation column 110 with a steam reboiler 112. The distillation columns 96 and 110 are provided with reflux condensers and associated piping, which are not shown in FIG. 1.

From the wax processing stage 24 a $C_5$-$C_{10}$ naphtha by-product line 114, a $C_{11}$-$C_{19}$ diesel by-product line 116, a heavier than diesel hydrocarbon line 118 and one or more speciality lubricant base oils and/or wax cuts product line 120 lead to various destinations, as will be described in more detail hereinafter.

The steam reboiler 98 of the distillation column 96 is fed by a steam line 121. From the distillation column 96, a hydrocarbon condensate heavy ends line 122, a diesel line 124, a $C_9$-$C_{13}$ hydrocarbon line 126, a $C_1$-$C_8$ naphtha line 128 and a light gases line 130 lead to various destinations, which will also be described in more detail hereinafter.

The $C_5$-$C_8$ naphtha line 128 and the tail gas hydrocarbon condensate line 74 or the 1-hexene lean hydrocarbon line 75, as the case may be, feed into the second fluidised catalytic cracker riser reactor 106. The $C_9$-$C_{13}$ hydrocarbon line 126 leads into the first fluidised catalytic cracker riser reactor 104.

In another embodiment of the invention (not shown), if desired, a 1-hexene recovery stage is provided to extract 1-hexene from the $C_5$-$C_8$ naphtha prior to feeding the $C_5$-$C_8$ naphtha into the second fluidised catalytic cracker riser reactor 106.

A linear alkyl-benzene product line 136 leads from the oxygenate removal and olefin conversion stage 102. A benzene feed line 138 provides the benzene that reacts with the olefins in stage 102 to produce the linear alkylbenzene.

The catalyst of the first and second fast catalytic cracker riser reactors 104, 106 passes to a regenerator 105 that is supplied with air by means of an air feed line 140. From the top of these units, an olefin containing product line 142 and a gasoline containing product line 144 leave. A flue gas line 146 also leaves the regenerator 105.

The gasoline containing product line 144 leads into the cooler 108, from where it leads into the distillation column 110. A light gases line 111, a gasoline product line 148, a diesel line 150 and a heavy oil product line 152 leave the distillation column 110, the line 150 leading into the diesel hydrotreater stage 100. The line 111 leads into the line 142.

A hydrogen feed line 154 leads into the diesel hydrotreater stage 100, together with the diesel line 124 from the distillation column 96 and the diesel line 150 from the distillation column 110. A diesel product line 156 leaves the diesel hydrotreater stage 100 and is joined by the $C_{11}$-$C_{19}$ diesel by-product line 116 from the wax processing stage 24.

The heavier than diesel hydrocarbon line 118 from the wax processing stage 24, and the hydrocarbon heavy ends line 122 from the distillation column 96 feed into the first fast catalytic cracker riser reactor 104. Similarly, the heavy oil line 58 from the washing column 46 feeds into the first fast catalytic cracker riser reactor 104.

In use, a gaseous synthesis gas feedstock comprising hydrogen and carbon monoxide is fed along the gaseous feedstock line 18 and optionally heated in the heater 14, before entering the first Fischer-Tropsch reaction stage 12. This gaseous synthesis gas feedstock, when derived from natural gas, is typically obtained by subjecting the natural gas to a partial oxidation reforming step or autothermal reforming step operating with a low steam to carbon ratio to produce a synthesis gas with an $H_2$:CO ratio of less than 2.4. The first reaction stage 12 comprises one or more slurry bed reactors, operating at a pressure typically between 10 bar and 50 bar and a temperature typically between 220° C. and 260° C. These three-phase slurry bed reactors each include a slurry bed of a solid particulate precipitated promoted iron Fischer-Tropsch catalyst suspended in liquid hydrocarbon product (mostly wax). The gaseous synthesis gas feedstock enters the slurry beds at a low level and the hydrogen and carbon monoxide react catalytically as they pass upwardly through each slurry bed, thereby to form liquid hydrocarbon products and gaseous products. The liquid product is withdrawn along the liquid product line 22 and the gaseous products and unreacted feedstock leave the first reaction stage 12 along the gaseous product line 20. The operation of a three-phase low temperature catalytic Fischer-Tropsch reaction stage, such as the reaction stage 12, is known to those skilled in the art and will thus not be described in any further detail herein.

The gaseous products, typically at a temperature of up to 250° C., enter the cooler 16 and are cooled in conventional fashion to a temperature of between about 30° C. and about 80° C., e.g. 70° C., before being fed into the separator 26. In the separator 26, three-phase separation takes place, with condensed reaction water being removed along the reaction water line 28, hydrocarbon condensate, which includes a $C_9$-$C_{13}$ fraction containing olefins, being removed along the hydrocarbon condensate line 30, and first stage tail gas leaving the separator 26 along the first stage tail gas line 32.

If desired, a portion of the first stage tail gas may be recycled to the first Fischer-Tropsch reaction stage 12, by means of the first stage tail gas recycle line 34 and the compressor 36. When used, the ratio of the gaseous feedstock to first stage tail gas recycle will typically be about 1:1 but is unlikely to exceed about 2:1.

From the separator 26, the first stage tail gas is optionally heated in the heater 40 before entering the second Fischer-Tropsch reaction stage 42. However, prior to entering the second Fischer-Tropsch reaction stage 42, the composition of the first stage tail gas is adjusted to obtain a ratio of $H_2/(2CO+3CO_2)$ of between about 1 and 1.05. In the embodiment of the process of the invention shown in FIG. 1, this ratio is adjusted by the addition of an $H_2$ rich gas along the $H_2$ rich gas line 38 to the first stage tail gas line 32.

The second Fischer-Tropsch reaction stage 42 typically comprises one or more two-phase fluidised bed reactors operating at a high Fischer-Tropsch synthesis reaction temperature typically between 320° C. and 350° C. In these fluidised bed reactors, the carbon monoxide and hydrogen react to form gaseous hydrocarbons which leave the second Fischer-Tropsch reaction stage 42 along the gaseous product line 44. As is the case with the first Fischer-Tropsch reaction stage 12, the catalyst used in the second Fischer-Tropsch reaction stage 42 is a promoted iron catalyst but will typically be a fused catalyst. The operation of a high temperature Fischer-Tropsch reaction stage, such as the second Fischer-Tropsch reaction stage 42, is also well known to those skilled in the art and will not be described in further detail.

The gaseous hydrocarbons from the second Fischer-Tropsch reaction stage 42 enter the washing column 46 which uses heavy oil, and hydrocarbon condensate from the separator 48, as a washing liquid. The heavy oil is circulated by means of the pump 52, with the cooler 54 removing heat introduced by the gaseous hydrocarbons from the second Fischer-Tropsch reaction stage 42.

Gaseous hydrocarbons passing through the washing column 46 leave the washing column 46 by means of the gaseous product line 44 and are cooled in the cooler 50 before entering the separator 48. Before entering the separator 48, the gaseous hydrocarbons are thus cooled to a temperature of between about 30° C. and 80° C., e.g. about 70° C. In the cooler 50 and the separator 48, reaction water condenses and is removed along the reaction water line 60. Some hydrocarbons also condense to form a hydrocarbon condensate, which is removed along the hydrocarbon condensate line 62. The remaining gaseous hydrocarbons leave the separator 48 as second stage tail gas, along the second stage tail gas line 64.

In the second Fischer-Tropsch reaction stage 42, preferably at least 85% of the CO and $CO_2$ entering the second Fischer-Tropsch reaction stage 42 is converted to hydrocarbons. In order to achieve such high conversion rates, a portion of the second stage tail gas is recycled, by means of the second stage tail gas recycle line 65 and the compressor 67, to the second Fischer-Tropsch reaction stage 42. Typically, the ratio of first stage tail gas fed to the second Fischer-Tropsch reaction stage 42, to second stage recycle tail gas, is about 1:1 but is unlikely to exceed 2:1.

The second stage tail gas which is not recycled to the second Fischer-Tropsch reaction stage 42, is refrigerated in the refrigeration stage 68 typically to a temperature of about 5° C. The refrigerated second stage tail gas then enters the separator 70 to be separated into an aqueous tail gas condensate removed along the tail gas aqueous condensate line 72, a tail gas hydrocarbon condensate removed along the tail gas hydrocarbon condensate line 74, and wet tail gas removed along the wet tail gas line 76.

The wet tail gas from the separator 70 is fed to the $CO_2$ removal stage 76.1. Separated $CO_2$ is removed along line 76.2. The wet tail gas is then dried in the dryer 78 and fed by means of the dry tail gas line 80 to the heat exchanger 82 where it is cooled further before passing through an expansion turbine 84 (other expansion or cooling techniques may instead be used), which causes the temperature of the dry tail gas to drop to about −80° C. This cold dry tail gas is fed into the separator 86, where it is separated into light liquid hydrocarbons, typically $C_2$+hydrocarbons but possibly including methane, which are removed along the light hydrocarbon line 88, and a hydrocarbon lean hydrogen rich tail gas which is removed along the lean tail gas line 90 and passed through the heat exchanger 82 in heat exchange relationship with the dry tail gas in the dry tail gas line 80. Other more complex heat exchange relationships may also be used.

The light hydrocarbons in the light hydrocarbon line 88 can be further separated by separation methods known to those skilled in the art to produce ethylene, propylene and butylene products and $C_1$-$C_4$ paraffin by-products. The light paraffinic by-product gas can optionally be used in a gas turbine for power generation and/or in a fuel gas system for process and utility heating purposes. The hydrocarbon lean hydrogen rich tail gas in line 90 can be optionally partially recycled, by means of the optional recycle line 92, to the first stage tail gas line 32 supplementing or even replacing the $H_2$ rich gas fed along line 38.

The liquid product removed from the first Fischer-Tropsch reaction stage 12 typically predominantly comprises wax, i.e. $C_{19}$+liquid hydrocarbons. In the wax processing stage 24, using methods known to those skilled in the art (typically hy-droprocessing and fractionation), this liquid product is converted into a $C_5$-$C_{10}$ naphtha by-product, which is withdrawn along the $C_5$-$C_{10}$ naphtha by-product line 114, a $C_{19}$-$C_{19}$ diesel by-product which is removed along the $C_{19}$-$C_{19}$ diesel by-product line 116, a heavier than diesel hydrocarbon product which is removed along the heavier than diesel hydrocarbon line 118 and a plurality of speciality lubricant base oils and/or high value wax cuts, as indicated by reference numeral 120. If desired, a portion or all of the liquid product can be fed to the first fluidised catalytic cracker riser reactor 104, without passing through the wax processing stage 24.

The hydrocarbon condensate from the separator 48 and the hydrocarbon condensate from the separator 26 are joined by means of the flow lines 62 and 30 and fed to the distillation column 96. The distillation column 96 makes use of a steam reboiler 98 fed by the steam line 121 to distil the hydrocarbon condensate into various fractions. Hydrocarbon heavy ends are removed from the distillation column 96 by means of the hydrocarbon heavy ends line 122 and fed to the first fluidised catalytic cracker riser reactor 104. A diesel fraction is produced (typically with the use of a side stream stripper which is not shown), removed along the diesel line 124 and fed to the diesel hydrotreater stage 100. A $C_9$-$C_{13}$ hydrocarbon fraction is removed along the $C_9$-$C_{13}$ hydrocarbon line 126 and fed to the first fluidised catalytic cracker riser reactor 104 and a $C_5$-$C_8$ naphtha fraction is removed and fed by means of the $C_5$-$C_8$ naphtha line 128 to the second fluidised catalytic cracker riser reactor 106. Light gases from the distillation column 96 are removed along the light gases line 130 and can be combined with the lean tail gas in the fuel line 94 for process and utility heating purposes.

In the oxygenate removal and olefin conversion stage 102, the $C_9$-$C_{13}$ olefin fraction from the separator 26 is alkylated to produce linear alkyl-benzene (LAB), which is removed by means of the linear alkyl-benzene product line 136. The remaining hydrocarbon condensate material proceeds along line 30 to the distillation column 96 where it may be fed to the column at the appropriate point or combined with the product streams from this column as appropriate. Alternatively, paraffins may be separated and sold as final products.

The second fluidised catalytic cracker riser reactor 106 is operated to produce maximum propylene yield and is fed with tail gas hydrocarbon condensate from the separator 70 (which may be 1-hexene lean) and the $C_5$-$C_8$ naphtha stream 128 from the distillation column 96. Instead, the naphtha can be processed together with the tail gas hydrocarbon condensate in line 74 to recover $C_5$-$C_8$ alpha olefin products, with the balance of the material being sent to the second fluidised catalytic cracker riser reactor 106. Such alpha olefins can be recovered by separation processes known to those skilled in the art and are useful as co-monomers for the production of plastics.

Air is fed into the fluidised catalytic cracker regenerator 105 by means of the air feed line 140, for purposes of catalyst regeneration. In the reactors 104, 106, known catalyst/gas separation systems are used in combination with a fluidised bed.

An olefin containing product leaves the second fluidised catalytic cracker riser reactor 106 by means of the olefin containing product line 142. This gaseous olefin containing product may be combined with the second stage tail gas in line 64 or possibly more preferred with the dry tail gas in the dry tail gas line 80 in order to recover $C_2+$ hydrocarbons.

The first fluidised catalytic cracker riser reactor 104 is operated to provide maximum gasoline yield. From the first fluidised catalytic riser reactor 104, a gasoline containing product is thus fed along the gasoline containing product line 144 to the cooler 108 and from there into the distillation column 110. The distillation column 110 uses a steam reboiler 112 fed by a steam line 113 to produce a small heavy oil by-product removed along line 152, a diesel product removed by the diesel line 150, a gasoline product removed by means of the gasoline product line 148 and light gases in line 111 that may be combined with the product from the second fluidised catalytic riser reactor in line 142.

Catalyst from the reactors 104, 106 passes to the regenerator 105 which produces a flue gas which is vented to atmosphere via line 146

The heavy oil by-product in line 152 from the distillation column 110 may be treated in several ways known to persons skilled in the art of crude oil refining.

The first fast catalytic cracker riser reactor 104 is also fed with heavy oil from the washing column 46 by means of the heavy oil line 58, heavier than diesel hydrocarbon from the wax processing stage 24, which is fed along the heavier than diesel hydrocarbon line 118, and the hydrocarbon heavy ends from the distillation column 96 fed along the line 122. If desired, this feed to the first fast catalytic cracker riser reactor 104 may be supplemented with crude oil derived feed material to optimise the capacity of the fast catalytic cracker riser reactor 104.

The diesel from the distillation column 96, fed by means of the diesel line 124 into the diesel hydrotreater stage 100, is treated with hydrogen, fed by means of the hydrogen feed line 154, to produce a diesel product which is removed by means of the diesel product line 156. The diesel hydrotreater stage 100 is also fed with diesel from the distillation column 110, by means of the diesel line 150. The $C_{11}$-$C_{19}$ diesel by-product line 116 from the wax processing stage 24 joins the diesel product line 156.

Instead of using an $H_2$ rich gas to adjust the composition of the first stage tail gas in the first stage tail gas line 32, the composition can be adjusted by removing excess $CO_2$ from the first stage tail gas. Alternatively, steam may be added to the first stage tail gas line 32, whereafter the combined steam and first stage tail gas is heated and fed to a water gas shift reactor (not shown) to allow the water gas shift reaction to take place. This technology is well known to those skilled in the art and will typically be used if the synthesis gas feedstock is coal derived. As a result of the water gas shift reaction, the $H_2$ and $CO_2$ concentration in the first stage tail gas will be increased to provide a $H_2$:CO concentration of at least 2.1, preferably 2.3. The gas from the water gas shift reactor can be cooled whereafter excess $CO_2$ can be removed in a conventional $CO_2$ removal stage (not shown) to provide first stage tail gas suitable for feeding to the second Fischer-Tropsch reaction stage 42. Typically, in this configuration, the hydrocarbon lean but $H_2$ rich tail gas in the recycle line 92 will be returned to the first stage tail gas downstream of $CO_2$ removal. As will be appreciated, a slipstream of the first stage tail gas may be employed for composition adjustment purposes.

Alternatively, the addition of an $H_2$ rich gas may be combined with a water gas shift reactor (not shown) to affect the reverse water gas shift reaction to adjust the composition of the first stage tail gas. The technology used is similar to that employed for the forward water gas shift reaction. $H_2$ and $CO_2$ are reacted to form water and CO. It is preferred to remove water formed in the reverse water gas shift reaction prior to feeding the composition adjusted first stage tail gas to the second Fischer-Tropsch reaction stage 42. This option is advantageously used in combination with partial recycle of $CO_2$ from the $CO_2$ removal stage 76.1 to the first stage tail gas in line 32 (not shown).

Referring to FIG. 2 of the drawings, reference numeral 200 generally indicates another embodiment of a process in accordance with the invention for synthesising hydrocarbons. The process 200 is to a large extent similar to the process 10 and, unless otherwise indicated, the same reference numerals are used to indicate the same or similar features.

Unlike the process 10, the process 200 does not include catalytic cracker riser reactors 104, 106, a cooler 108, or a distillation column 110. Instead, the process 200 includes distillation columns 202 and 204 and a COD unit (Conversion of Olefins to Distillate unit) 206.

The heavy oil line 58 from the washing column 46 leads into the distillation column 202. A heavies line 210 leads from a bottom of the distillation column 202 into the hydrocarbon heavy ends line 122 which leads from the distillation column 96 to the wax processing stage 24. A diesel line 212 leads from the distillation column 202 into the diesel line 124 running between the distillation column 96 and the diesel hydrotreater stage 100.

The hydrocarbon condensate line 62 from the separator 48 leads into the distillation column 204. A diesel line 214 leads from the bottom of the distillation column 204 and joins the diesel line 212 from the distillation column 202. A lights line 216 and a $C_5$-$C_9$ line 218 leave the distillation column 204, the $C_5$-$C_9$ line 218 joining the tail gas hydrocarbon condensate line 74 from the separator 70 before feeding into an optional 1-hexene recovery stage 103.

A $C_5$-$C_8$ line 220 leads from the distillation column 96 and is joined by the 1-hexene lean hydrocarbon line 75 from the 1-hexene recovery stage 103 before leading into the COD unit 206.

In another embodiment of the invention (not shown), if desired, a 1-hexene recovery stage is provided to extract 1-hexene from the $C_5$-$C_8$ fraction in line 220 prior to feeding the $C_5$-$C_8$ fraction into the COD unit 206.

A naphtha line 222 and a diesel line 224 leave the COD unit 206, the diesel line 224 joining the diesel line 124 and the naphtha line 222 being joined by the $C_5$-$C_{10}$ naphtha by-product line 114 from the wax processing stage 24.

The wax processing stage 24 has a recycle line 226 and a lights line 228 whereas the oxygenate removal and olefins conversion stage 102 has an n-paraffin line 230.

In use, the process 200 is operated similar to the process 10. However, the process 200 produces fuel gas, LP gas, light olefins, naphtha, diesel, linear alkyl benzene, base oils and optionally comonomers. No gasoline product is produced.

In the process 200, the heavy oil from the washing column 46 is fed by means of the heavy oil line 58 into the distillation column 202 where it is separated into a heavies fraction and a diesel fraction. The heavies fraction is sent to the wax processing stage 24 by means of the heavies line 210 whereas the diesel fraction is sent to the diesel hydrotreater stage 100 by means of the diesel line 212.

The hydrocarbon condensate from the separator 48 is fed to the distillation column 204 where it is distilled into a diesel fraction, a $C_5$-$C_9$ hydrocarbon fraction and a lights fraction. The lights fraction is removed by means of the lights line 216 and the diesel fraction is removed by means of the diesel line 214 for feeding to the diesel hydrotreater stage 100. The $C_5$-$C_9$ hydrocarbon fraction (naphtha) is removed by means of the $C_5$-$C_8$ line 218 and joins up with the tail gas hydrocarbon condensate in the tail gas hydrocarbon condensate line 74 coming from the separator 70, before being fed to the 1-hexene recovery stage 103.

The distillation column 96 produces a $C_5$-$C_8$ hydrocarbon fraction which is removed by means of the $C_5$-$C_8$ line 220. The 1-hexene lean hydrocarbon stream (line 75) from the 1-hexene recovery stage 103 joins the $C_5$-$C_8$ hydrocarbon stream from the distillation column 96 before being fed into the COD unit 206. In the COD unit 206, the olefin content of a $C_5$-$C_9$ naphtha cut is oligomerised using a zeolite catalyst to add to the diesel product from the distillation columns 202, 204 and 96 (by means of the diesel line 224). Naphtha is removed from the COD unit 206 by means of the naphtha line 222 and joins with the naphtha by-product in the line 114 from the wax processing stage 24.

In the wax processing stage 24, which receives heavies from the distillation column 202 and the distillation column 96, the heavies is recycled to extinction by means of the recycle line 226. Lights from the wax processing stage 24 (line 228), the distillation column 96 (line 130) and the distillation column 204 (line 216) can either by used as fuel gas or combined with the wet tail gas being fed to the dryer 78. Although not shown in FIG. 2, the dry tail gas leaving the dryer 78 along line 80 can be worked up in similar or identical fashion to the dry tail gas of the process 10, to produce a light hydrocarbon stream (LP gas) and fuel gas.

Unlike in the process 10, the oxygenate removal and olefins conversion stage 102 receives a $C_9$-$C_{13}$ olefins feed from the distillation column 96 to produce linear alkyl benzene and an n-paraffin product stream. If desired, the n-paraffins coming from the olefin separation and conversion stage 102 can be fed to the diesel hydrotreater stage 100.

EXAMPLE

The process 200 was simulated mathematically using conventional process simulation software. The simulated process 200 included first stage tail gas composition adjustment using the addition of $H_2$ rich gas together with $CO_2$ recycle from the second Fischer-Tropsch reactor stage tail gas $CO_2$ removal and reverse water gas shift at 500° C.

The following process parameters were used: The first reaction stage overall CO and $H_2$ conversion and per pass CO and $H_2$ conversion was 62% and 35% respectively. The ratio of gaseous feedstock to first stage tail gas recycle was 1:1. The second reaction stage overall CO and $CO_2$ conversion and per pass CO and $CO_2$ conversion was 69% and 36% respectively. The ratio of second reaction stage tail gas recycle to the composition adjusted first stage tail gas was 1.2:1. The feed to the first reaction stage had an $H_2$/CO ratio of 1.64. The adjusted first stage tail gas $H_2$/(2CO +3CO) ratio was 0.93.

The process achieved an overall CO and $CO_2$ conversion of 77% and a methane selectivity of 17%. The wax product from the first reactor stage comprised 13% of the overall hydrocarbons produced.

In addition to the wax product, hydrocarbon products with the following mass breakdown were produced:

| | |
|---|---|
| Fuel gas | 29% |
| Ethylene | 4% |
| Propylene | 9% |
| LPG | 3% |
| Naphtha | 16% |
| Diesel | 37% |
| Ethanol | 2% |

Typically, the tail gas from a low temperature Fischer-Tropsch reaction stage contains $C_5$- hydrocarbons in quantities too small to justify the costs of recovery. Advantageously, in the process of the invention, these will pass through to the high temperature Fischer-Tropsch reaction stage, which typically produces significant quantities of $C_5$- hydrocarbons, and thus mix with the gaseous products from the high temperature Fischer-Tropsch reaction stage. These $C_5$- hydrocarbons from the low temperature Fischer-Tropsch reaction stage are thus recovered in the processes and methods known to those skilled in the art usually used to recover $C_2$+ hydrocarbons from high temperature Fischer-Tropsch reaction stages.

Advantageously, for the process of the invention, high low temperature Fischer-Tropsch reactor productivity is attained by operating with a per pass conversion between about 30% and about 50%, with or without tail gas recycle. With the low temperature Fischer-Tropsch reaction stage being followed by the high temperature Fischer-Tropsch reaction stage, unreacted hydrogen and carbon monoxide are not lost or wasted, but in the high temperature Fischer-Tropsch reaction stage is converted in a low cost conversion option for residual reactants remaining after using a single low temperature Fischer-Tropsch reaction stage. Furthermore, the catalyst consumption for the high temperature Fischer-Tropsch reaction stage will be particularly low due to the absence of catalyst poisons and the favourable feed gas composition (high hydrogen partial pressure) that inhibits carbon formation.

The value of the low temperature Fischer-Tropsch derived products of the process of the invention is typically higher than the value of the high temperature Fischer-Tropsch derived products. Furthermore, the low temperature Fischer-Tropsch derived products obtained from promoted iron catalyst are typically more valuable than those obtained using the low temperature Fischer-Tropsch process with supported cobalt catalysts, due to the higher hard wax selectivity, lower methane selectivity and higher olefin content in the $C_2$ to $C_{13}$ hydrocarbon product streams.

As a result of economy of scale advantages, the costs of producing all the main non-fuel products using the process of the invention is potentially lower than the cost from competing prior art processes known to the Applicant, provided that the feedstock coal or natural gas price is not excessive. The cost of producing the gasoline and diesel fuels is also competitive unless crude oil prices are exceptionally low. As capital costs are higher for a coal fed facility than for a natural gas fed facility, a natural gas feed is preferred for the process of the invention. However, in the case where the process is coal fed, electrical power export is a significant by-product.

The main products from the process of the invention may include lubricant base oils and/or high value wax products, propylene, ethylene, linear alkyl-benzene, and high quality (sulphur-free) gasoline and diesel fuels. Optional by-products may include 1-hexene and oxygenated hydrocarbons, predominantly ethanol, methanol, acetone and methyl-ethyl ketone.

The invention claimed is:

1. A process for synthesizing hydrocarbons, which process includes feeding a gaseous feedstock comprising hydrogen and carbon monoxide, into a first Fischer-Tropsch reaction stage which is a three-phase low temperature catalytic Fischer-Tropsch reaction stage operating at a temperature less than 280° C. and a pressure in the range 10 to 50 bar;

allowing the hydrogen and carbon monoxide partially to react catalytically in the first reaction stage to form hydrocarbons;

feeding at least a portion of a tail gas which includes unreacted hydrogen and carbon monoxide obtained from the first reaction stage, into a second Fischer-Tropsch reaction stage which is a two-phase high temperature catalytic Fischer-Tropsch reaction stage operating at a temperature of at least 320° C. and a pressure in the range 10 to 50 bar; and allowing the hydrogen and carbon monoxide at least partially to react catalytically in the second reaction stage to form gaseous hydrocarbons.

2. The process as claimed in claim 1, in which the first reaction stage includes a slurry bed of a solid particulate Fischer-Tropsch catalyst suspended in a carrier liquid, with the gaseous feedstock entering the slurry bed at a low level, and in which the hydrogen and carbon monoxide react catalytically as they pass upwardly through the slurry bed, thereby to form liquid hydrocarbon products and gaseous products, with the liquid hydrocarbon products thus constituting the carrier liquid of the slurry bed.

3. The process as claimed in claim 1, in which the tail gas from the first reactor stage includes $CO_2$ and which includes adjusting a ratio of $H_2/(2CO+3CO_2)$ in the first stage tail gas, prior to feeding the adjusted first stage tail gas to the second reaction stage.

4. The process as claimed in claim 3, in which the ratio $H_2/(2CO+3CO_2)$ in the adjusted first stage tail gas fed to the second reaction stage is between 0.8 and 1.05.

5. The process as claimed in claim 3, in which the ratio $H_2/(2CO+3CO_2)$ is adjusted by the addition of an $H_2$ rich gas to the first stage tail gas.

6. The process as claimed in claim 3, in which the ratio $H_2/(2CO+3CO_2)$ is adjusted by removing excess $CO_2$ from the first stage tail gas.

7. The process as claimed in claim 3, in which the ratio $H_2/(2CO+3CO_2)$ is adjusted by shifting some of the CO in the first stage tail gas by reaction with steam to produce $H_2$ and $CO_2$, in accordance with the water gas shift reaction $CO+H_2O \leftrightarrows CO_2+H_2$.

8. The process as claimed in claim 3, in which the ratio $H_2/(2CO+3CO_2)$ is adjusted by converting excess $CO_2$ to CO using the reverse water gas shift reaction $CO_2+H_2 \leftrightarrows CO+H_2O$.

9. The process as claimed in claim 1, in which the Fischer-Tropsch catalyst used in the first reaction stage is a shifting catalyst, and in which the first reaction stage is operated with a low per pass conversion of CO and $H_2$ of between about 30% and about 50%.

10. The process as claimed in claim 1, in which overall first stage CO and $H_2$ conversion is no more than 65% and overall second stage CO and $CO_2$ conversion is at least 65%.

11. The process as claimed in claim 1, which includes recycling some of the first stage tail gas to the first reaction stage, withdrawing gaseous hydrocarbons and any unreacted hydrogen, unreacted carbon monoxide and any gaseous by-products from the second reaction stage and separating these gases into one or more condensed liquid hydrocarbon streams, a reaction water stream and a second stage tail gas, and recycling some of the second stage tail gas to the second reaction stage.

12. The process as claimed in claim 1, which includes withdrawing liquid hydrocarbon products and gases and vapours from the first reaction stage, cooling the gases and vapours to condense liquid hydrocarbons and reaction water present therein and to produce tail gas including unreacted hydrogen and carbon monoxide and $C_5-$ hydrocarbons for feeding to the second Fischer-Tropsch reaction stage.

13. The process as claimed in claim 12, in which the $C_5-$ hydrocarbons which are fed with the tail gas from the first reaction stage to the second reaction stage, are recovered, with $C_5-$ hydrocarbons formed in the second reaction stage, from the gaseous hydrocarbons obtained from the second reaction stage.

14. The process as claimed in claim 12, which includes treating the condensed hydrocarbons from the first reaction stage to provide a $C_9-C_{13}$ hydrocarbon fraction which includes olefins.

15. The process as claimed in claim 1, in which oxygenates are removed from an olefins containing stream and the olefins are alkylated to produce linear alkyl-benzene as a product.

16. The process as claimed in claim 13, in which the $C_5-$ hydrocarbons are treated to provide ethylene, propylene and butylene.

17. The process as claimed in claim 12, in which the liquid hydrocarbon products are worked up to produce one or more of diesel, naphtha, lubricants or speciality wax.

18. The process as claimed in claim 1, which produces olefins as an intermediate product and in which a COD unit is used to oligomerize the clefins to enhance diesel production.

19. The process as claimed in claim 1, in which a catalytic cracker is used to produce gasoline from heavier hydrocarbons produced as an intermediate product.

20. The process as claimed in claim 1, in which a $C_5+$ hydrocarbon stream is produced and in which 1-hexene is recovered from the $C_5+$ hydrocarbon stream.

\* \* \* \* \*